(12) United States Patent
Burgmeier et al.

(10) Patent No.: US 6,989,025 B2
(45) Date of Patent: Jan. 24, 2006

(54) EXTRUDED TUBING WITH DISCONTINUOUS STRIPING

(75) Inventors: Robert Burgmeier, Plymouth, MN (US); Daniel J. Horn, Shoreview, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 474 days.

(21) Appl. No.: 10/264,706

(22) Filed: Oct. 4, 2002

(65) Prior Publication Data

US 2004/0068285 A1  Apr. 8, 2004

(51) Int. Cl.
*A61F 2/06* (2006.01)

(52) U.S. Cl. .................... 623/1.11; 606/194
(58) Field of Classification Search ............. 606/108, 606/194; 623/1.11
See application file for complete search history.

(56) References Cited

U.S. PATENT DOCUMENTS

| | | | |
|---|---|---|---|
| 4,027,659 A | 6/1977 | Slingluff | 128/2 M |
| 5,047,045 A | 9/1991 | Arney et al. | 606/194 |
| 5,156,594 A | 10/1992 | Keith | 604/96 |
| 5,195,969 A | 3/1993 | Wang et al. | 604/96 |
| 5,226,899 A | 7/1993 | Lee et al. | 604/282 |
| 5,348,536 A | 9/1994 | Young et al. | 604/43 |
| 5,366,442 A | 11/1994 | Wang et al. | 604/103 |
| 5,549,552 A | 8/1996 | Peters et al. | 604/96 |
| 5,792,300 A | 8/1998 | Inderbitzen et al. | 156/244.13 |
| 5,810,867 A | 9/1998 | Zarbatany et al. | 606/191 |
| 5,824,173 A | 10/1998 | Fontirroche et al. | 156/86 |
| 5,834,032 A | 11/1998 | Song | 424/641 |
| 5,897,537 A | 4/1999 | Berg et al. | 604/282 |
| 5,938,653 A | 8/1999 | Pepin | 604/527 |
| 5,961,765 A | 10/1999 | Kastenhofer | 156/244.13 |
| 6,013,055 A | 1/2000 | Bampos et al. | 604/96 |
| 6,024,752 A | 2/2000 | Horn et al. | 606/192 |
| 6,030,405 A | 2/2000 | Zarbatany et al. | 606/191 |
| 6,136,258 A | 10/2000 | Wang et al. | 264/514 |
| 6,146,356 A | 11/2000 | Wang et al. | 604/96 |
| 6,190,356 B1 | 2/2001 | Bersin | 604/101.01 |
| 6,242,063 B1 | 6/2001 | Ferrera et al. | 428/35.2 |
| 6,284,333 B1 | 9/2001 | Wang et al. | 428/35.5 |
| 6,447,835 B1 | 9/2002 | Wang et al. | 427/2.24 |
| 6,482,348 B1 | 11/2002 | Wang et al. | 264/514 |
| 6,554,841 B1 | 4/2003 | Yang | 606/108 |
| 6,620,127 B2 | 9/2003 | Lee et al. | 604/96.01 |
| 2002/0010489 A1 * | 1/2002 | Grayzel et al. | 606/194 |
| 2003/0065352 A1 | 4/2003 | Yang et al. | 606/194 |
| 2003/0163148 A1 | 8/2003 | Wang et al. | 606/159 |

OTHER PUBLICATIONS

U.S. Appl. No. 09/965,765, filed Sep. 28, 2001, Wang.

\* cited by examiner

*Primary Examiner*—(Jackie) Tan-Uyen T. Ho
(74) *Attorney, Agent, or Firm*—Vidas, Arrett, Steinkraus

(57) ABSTRACT

A tubular member comprises a balloon having a body portion positioned between a first end and a second end. The body portion is constructed from an extruded matrix material and at least one stripe of a second extruded material. The at least one stripe is at least partially disposed within the matrix material. The proximal end and the distal end are constructed from the matrix material.

13 Claims, 5 Drawing Sheets

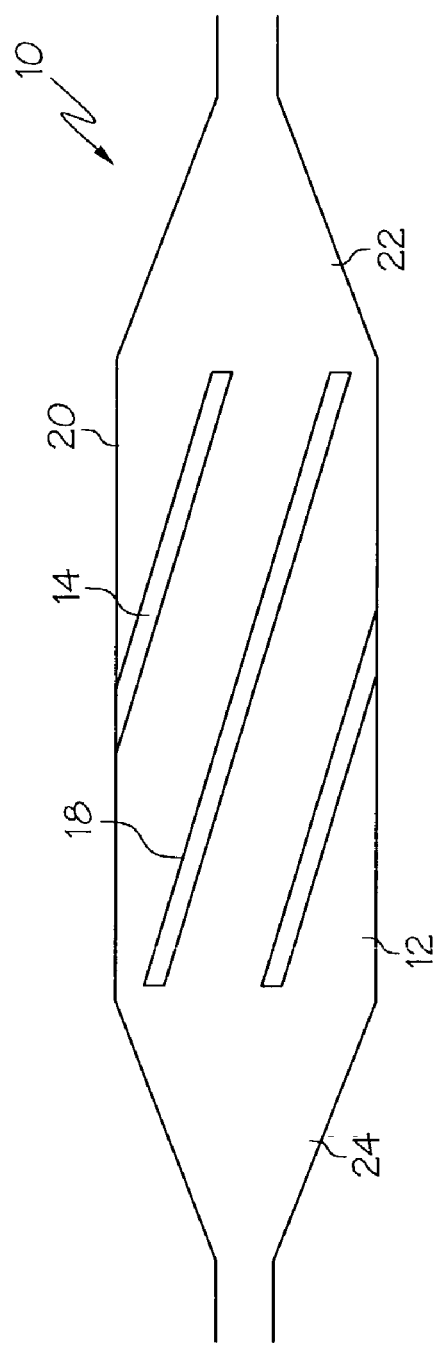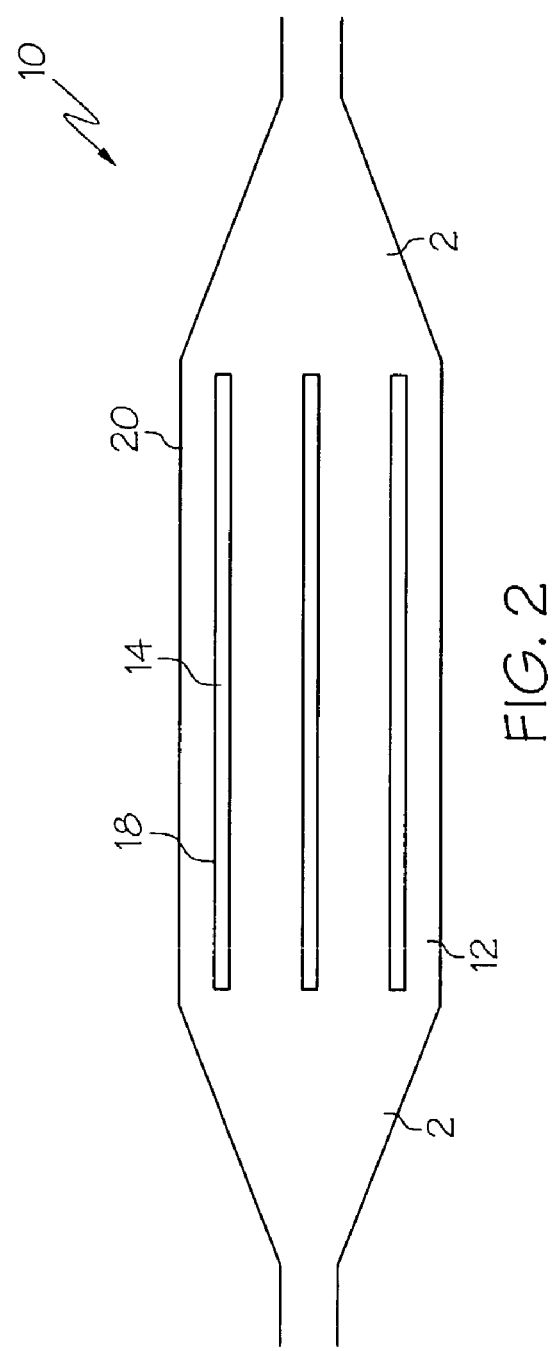

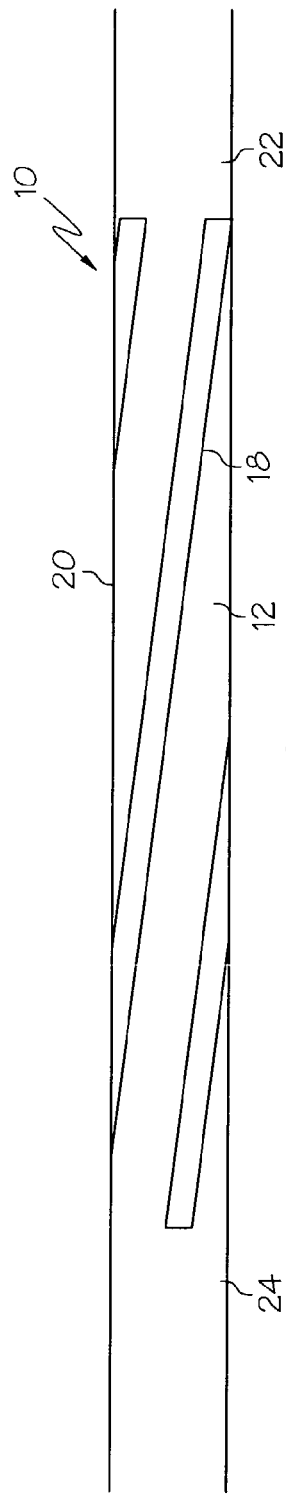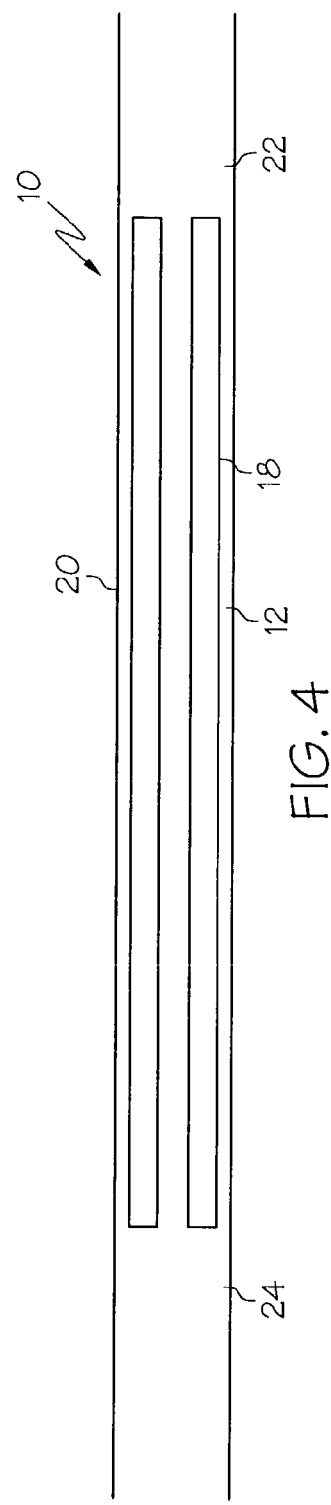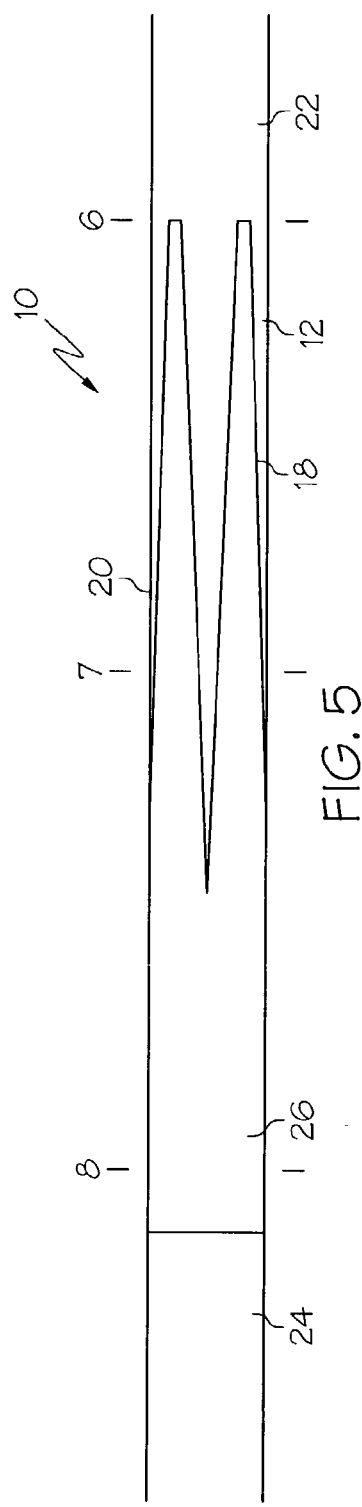

EXTRUDED TUBING WITH DISCONTINUOUS STRIPING

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

This invention relates to the field of intravascular medical devices and their methods of production, and more particularly to the field extruding tubular parisons for use in the manufacture of catheters and components thereof such as: angioplasty, balloon, neurological and guide catheters, among others, which may be used in various medical procedures such as percutaneous transluminal angioplasty (PTA), percutaneous transluminal coronary angioplasty (PTCA) as well as in procedures involving the placement of medicines and medical devices within the body.

Some embodiments of the invention are directed to all forms of catheters which may be advanced through a body lumen or vessel. Some examples of catheters are over-the-wire (OTW) catheters, such as are described in U.S. Pat. No. 5,047,045; single-operator-exchange (SOE) balloon catheters, such as are described in U.S. Pat. Nos. 5,156,594 and 5,549,552. Other examples of catheters which may utilize the unique features of the present invention are described in U.S. Pat. Nos. 5,938,653, 5,897,537, among others.

2. Description of the Related Art

Intravascular diseases are commonly treated by relatively non-invasive techniques such as PTA and PTCA. These angioplasty techniques typically involve the use of a balloon catheter. In these procedures, a balloon catheter is advanced through the vasculature of a patient such that the balloon is positioned proximate a restriction in a diseased vessel. The balloon is then inflated and the restriction in the vessel is opened. In other uses a catheter may be used to deliver an endoprosthesis such as a stent, graft, vena cava filter or other implantable device. Where an implantable device is to be delivered into a body lumen the catheter may include one or more inflatable portions or balloons.

Many procedures make use of a guide catheter positioned within the vascular system of a patient. The guide catheter assists in transporting a balloon dilation catheter, or other form of treatment device, to the portion of the vessel requiring treatment or inspection. The guide catheter is urged through the vasculature of the patient until its distal end is proximate the restriction. The balloon catheter may then be fed through a lumen in the guide catheter.

Whether an individual procedure utilizes a guide catheter or simply requires the use of a solitary dilatation or medical device delivery catheter, one catheter typically must possess a level of rigidity which will allow it to traverse tortuous pathways through blood vessels in a manner that minimizes trauma. The catheter must be capable of being advanced through the vascular system without folding or buckling despite application of longitudinal and/or rotational forces upon the catheter. Because many catheters have the desired rigidity, it may be desirable to incorporate flexibility and/or other desired characteristics into the catheter shaft. These sorts of improvements can be made through the application of one or more coatings to a catheter or portions thereof. For example, U.S. application Ser. No. 09/504,194 to Wang et al, filed Feb. 15, 2000, the entire content of which being incorporated herein by reference, describes a method of coating extruded polymeric tubes used in medical devices.

In some cases however, it may be desired to provide at least a portion of a catheter, particularly the distal tip with selected physical properties without the use of a coating. For example in U.S. application Ser. No. 09/965,765 to Yang et al, a distal tip of a catheter is preferably constructed from a coextrusion of at least two materials having different material characteristics such as hardness. The combination of materials is intended to provide the catheter tip with sufficient rigidity to avoid kinking and bending as it is advanced through a lumen, but to also provide the tip with sufficient flexibility so that the tip is less likely to cause trauma to vessel surfaces which it may contact.

The present invention seeks to provide a tubular member such as a balloon with desired physical characteristics by constructing the balloon or other member from a matrix of a first material with one or more stripes of at least one other material.

All US patents and applications and all other published documents mentioned anywhere in this application are incorporated herein by reference in their entirety.

Without limiting the scope of the invention, a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention includes many different embodiments. Some of the embodiments are directed to extruded tubular members for use in producing medical devices, particularly balloons.

In at least one embodiment, the invention is directed to a balloon constructed of a first material or matrix material that has stripes of either a stiffer or softer second material along the longitudinal or axial length of an extruded tubing.

The term "intermittent" as used herein in reference to the stripe(s) element, describes the shortened nature of the stripes relative to the length of the entire balloon. For example, an intermittent stripe as shown and described herein does not extend into the balloon cones.

In at least one embodiment the stripes are constructed from liquid crystal polymer material (LCP), nylon 12 and blends made therewith, polyester blends, etc.

In some embodiments the stripes increase in thickness and/or width for complete radial coverage of the at least a portion of the balloon body. By manipulating pull rates of the extruder, in some embodiments, the stripes could be increasingly stiffer or softer segments and/or be of increasingly longer or shorter lengths.

In at least one embodiment, the first material of the balloon completely encases the second material.

In at least one embodiment, at least a portion of the balloon comprises radially adjacent strips of matrix material and stripe material.

In various embodiments the intermittent striping of balloon tubing with at least two different materials provides a manufacturer with the ability to modify many characteristics of the balloon. Some examples of the properties that may be enhanced or otherwise altered through the use of stripes include, but are not limited to: kink resistance of the balloon as it is advanced through a vessel, balloon stiffness, radial strength of the balloon, etc.

In at least one embodiment, a balloon is provided with one or more substantially helically disposed stripes.

In at least one embodiment, a balloon is provided with one or more substantially longitudinally oriented stripes.

Additional details and/or embodiments of the invention are discussed below.

BRIEF DESCRIPTION OF THE SEVERAL VIEWS OF THE DRAWINGS

A detailed description of the invention is hereafter described with specific reference being made to the drawings.

FIG. 1 is a side view of an embodiment of the invention wherein a balloon is shown in an inflated state.

FIG. 2 is a side view of an embodiment of the invention wherein a balloon is shown in an inflated state.

FIG. 3 is a side view of the embodiment of the invention shown in FIG. 1, wherein the balloon is shown in an uninflated state.

FIG. 4 is a side view of the embodiment of the invention shown in FIG. 2, wherein the balloon is shown in an uninflated state.

FIG. 5 is a side view of an embodiment of the invention wherein the balloon is shown in the uninflated state.

DETAILED DESCRIPTION OF THE INVENTION

The present invention includes many different embodiments. For example, in FIGS. 1–4 embodiments of the invention are shown wherein different forms of a medical device, such as a balloon 10, are depicted. Balloon 10 may be any type of flexible and/or expandable tubular member capable of being inserted into a body lumen such as when mounted to a catheter. Numerous types and configurations of such medical devices are known and the term "balloon" as used herein is merely a convenient term used to designate all such devices.

In the various embodiments described herein, balloon 10 may be manufactured from at least two materials, namely, a first material or matrix material 12 and, a second material or stripe material 14. In the various embodiments shown and described herein the balloon 10 is formed by extrusion of a tubular parison comprised of matrix material 12 and stripe material 14. As may be seen in FIGS. 1–11, the stripe material 14 is produced as one or more stripes 18 relative to the matrix material 12 of the balloon 10.

In some embodiments, the stripe material 14 is characterized as having a physical characteristic, such as durometer value of hardness as measured on the Shore hardness scale, elasticity, etc., that is different that that of the matrix material 12.

Figure 10:
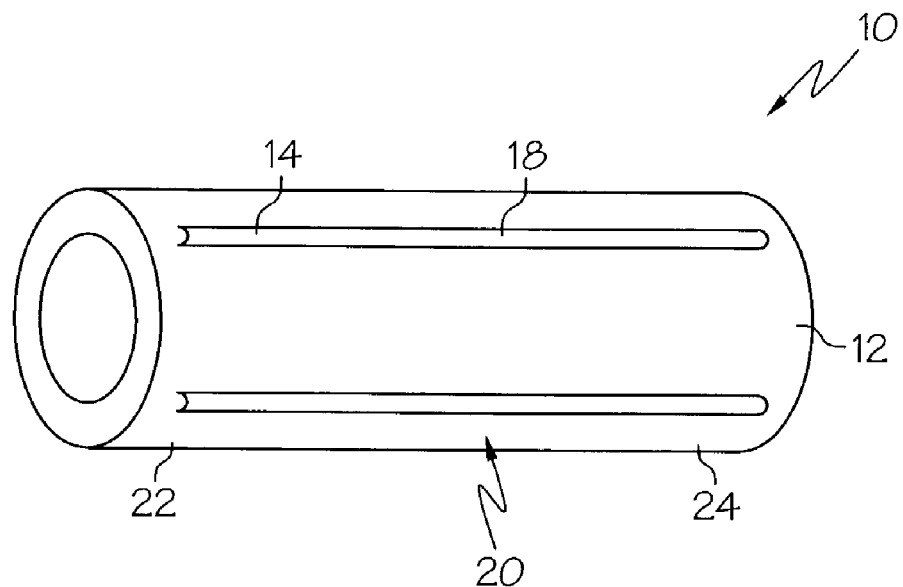
FIG. 10 is a side perspective view of an embodiment of the invention wherein at least a portion of the stripes protrude radially outward from the matrix material.
Figure 11:
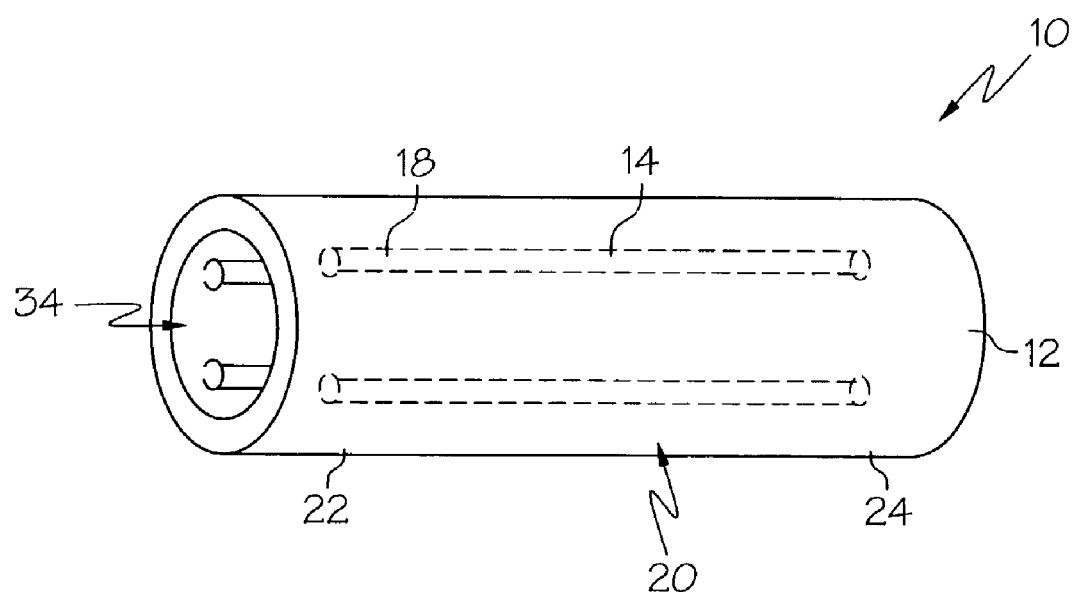
FIG. 11 is a side perspective view of an embodiment of the invention wherein at least a portion of the stripes protrude radially inward from the matrix material.

As indicated above in FIGS. 1 and 3 an embodiment of the balloon 10 is shown wherein the stripes 18 are helically wound about the body 20 of the balloon 10. In the various embodiments described herein, the stripes 18 may be disposed about the outside surface of the body 20, such as is shown in FIG. 10 or disposed about the inside surface of the body 20, such as is shown in FIG. 11. The stripes 18 are at least partially contained within the matrix material 14. In some embodiments, such as is shown in FIGS. 6–8, the stripes 18 are entirely contained within the matrix material 14 of the body 20.

FIGS. 2 and 4 show an embodiment wherein the stripes 18 extend in a substantially longitudinal manner relative to the body 20 of the balloon 10.

In the embodiments shown in FIGS. 1–4 it should be noted that the stripes 18 are positioned exclusively within the body 20 of the balloon and the stripes do not extend into the balloon cones or ends 22 and 24. Where the balloon 10 includes stripes 18 made of a softer material than the matrix material 12 the stripes may act to provide a more uniform inflation of the body 20 relative to the cones 22 and 24, particularly when a stent or other medical device (not shown) is disposed about the body 20 for delivery therefrom. The use of softer stripes 18 may also provide the balloon 10 with improved flexibility. The stripes 18 may also act to provide improved gripping of a stent or other medical device mounted on the body 20.

Figure 6:
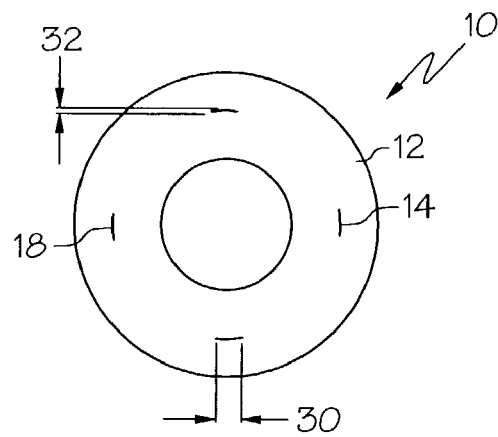
FIGS. 6–8 are cross-sectional views of sections of the embodiment shown in FIG. 5.
Figure 7:
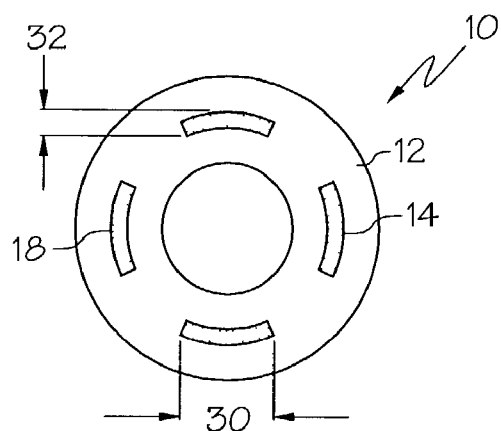
Figure 8:
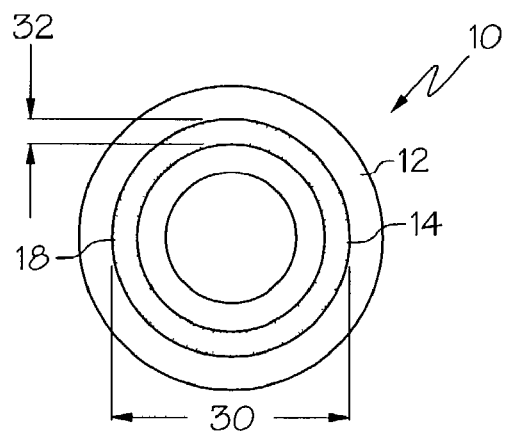
Figure 9:
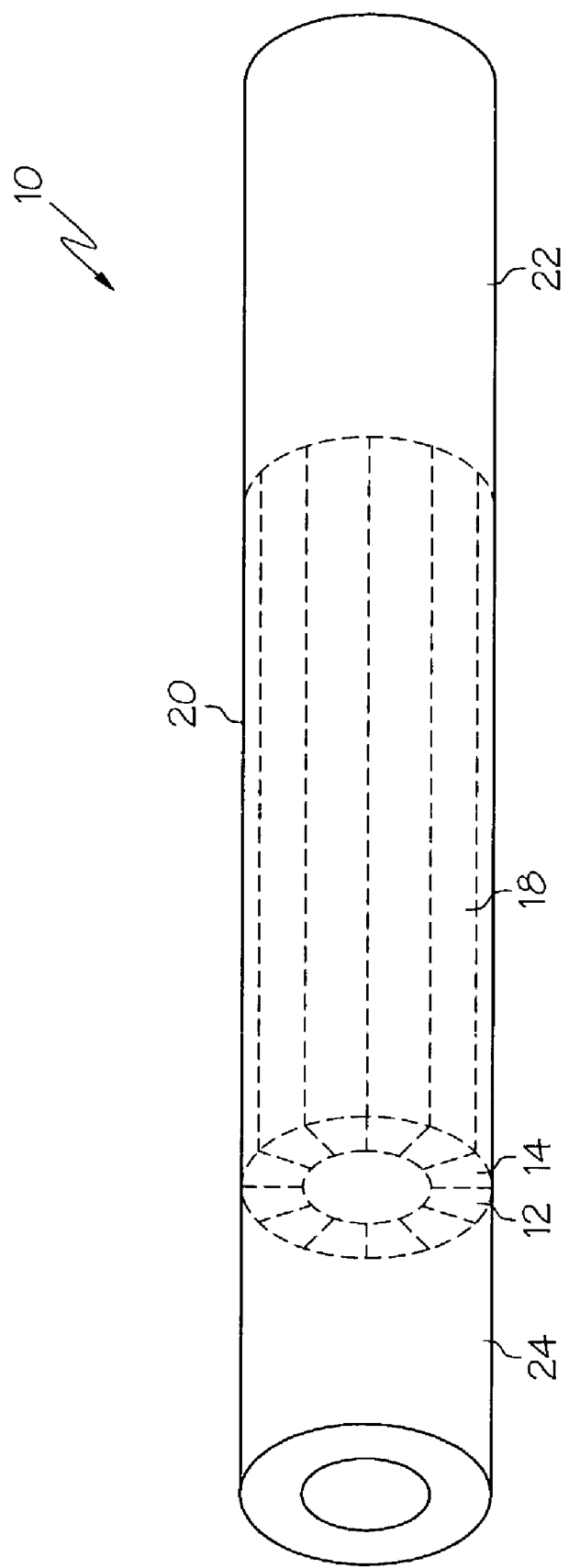
FIG. 9 is a side perspective view of an embodiment of the invention wherein the stripes are radially interspaced between portions of matrix material.

In the various FIGS. 1–11, the stripes 18 are formed during the extrusion process and may be varied in thickness and length by varying the speed and/or pull rate of the extruder, and/or by altering the size of the die. The extruder head may also be configured to provide the end product balloon 10 with stripes 18 that are disposed entirely within the matrix material 12, such as is shown in FIGS. 6–8; uniformly spaced between matrix material 12 of the same thickness, such as is shown in FIG. 9, positioned more radially outward relative to the matrix material 12, such as is shown in FIG. 10; and/or positioned more radially inward relative to the matrix material 12, such as is shown in FIG. 11.

In an embodiment of the invention such as is shown in FIG. 5, the stripes 18 extend the entire length of the balloon body 20 and gradually increasing in circumferential width as they travel from one end 22 toward the other 24. As the stripes approach the end 24 they join to form a complete ring 26 of stripe material 14. Such an embodiment is useful in providing a balloon 10 that will initially expand at one end verses the other.

As indicated above, the stripes 18 may be provided in a variety of thicknesses and widths depending on the particular speed, pull rate, and/or other extruder characteristics. As shown in FIGS. 6–8, the gradually increasing stripe of FIG. 5, may be provided with not only a varied circumferential width 30, but by modifying the extrusion characteristics as previously mentioned the cross-sectional width 32, among other aspects of the stripe 18 may also be varied as the stripes taper.

Alternatively, the balloon 10 may be provided with a body 20 comprised of stripes 18 having a uniform width and thickness interspaced between equally uniform portions of matrix material 12.

If it is desired to provide the balloon body with a textured surface, the stripes 18 may be extruded so that the stripes extend partially radially outward from the matrix material 12, such as is shown in FIG. 10. The embodiment shown in FIG. 10 is useful for providing a medical device such as a stent with an improved engagement surface about the balloon body 20, particularly when the stripe material 14 is relatively soft.

As is shown in FIG. 11, the balloon 10 may be formed such that the stripes 18 extend partially radially inward from the matrix material; that is to say the stripes 18 extend partially into the lumen 34 of the balloon 10.

In the various embodiments described herein, the stripes may comprise a wide variety of suitable stripe material(s) 12. For example, some strip materials, include but are not limited to LCP, nylon 12 and blends made therewith, polyester blends, etc. LCP materials suitable for use in the present invention are described in U.S. application Ser. No. 09/257,677 filed Feb. 25, 1999 and U.S. Pat. No. 6,242,063 The entire contents of both of these applications being hereby incorporated by reference.

Matrix material 12 and/or stripe material 14 may be selected from any of a variety of materials suitable for constructing the balloon 10. For example, one or both of the matrix material 12 and the stripe material 14 may be constructed from one or more compliant and/or non-compliant materials and combinations thereof. Compliant materials include low pressure, relatively soft or flexible polymeric materials, such as thermoplastic polymers, thermoplastic elastomers, polyethylene (high density, low density, intermediate density, linear low density), various co-polymers and blends of polyethylene, ionomers, polyesters, polyurethanes, polycarbonates, polyamides, poly-vinyl chloride, acrylonitrile-butadiene-styrene copolymers, poly-ether-polyester copolymers, and polyetherpolyamide copolymers. Suitable materials include a copolymer polyolefin material available from E.I. DuPont de Nemours and Co. (Wilmington, Del.), under the trade name Surlyn™ Ionomer and a polyether block amide available under the trade name PEBAX™. Non-compliant materials include relatively rigid of stiff high pressure polymeric materials, such as thermoplastic polymers and thermoset polymeric materials, poly(ethylene terephthalate) (commonly referred to as PET), polyimide, thermoplastic polyamide, polyamides, polyesters, polycarbonates, polyphenylene sulfides, polypropylene and rigid polyurethane. Further examples of balloon material may be found in U.S. Pat. No. 6,146,356.

Other materials suitable for use in the construction of the matrix material 12 and/or stripe material 14 include, nanocomposite materials, therapeutic agents such as drugs, drug delivery agents, bioactive coatings, cellular material, etc.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A tubular member comprising:
a balloon, the balloon having a body portion positioned between a first cone region and a second cone region, the body portion constructed from an extruded matrix material and at least one stripe of a second material at least partially contained within the matrix material, the second material being softer than the matrix material, the first cone region and the second cone region being constructed from the matrix material.

2. The tubular member of claim 1 wherein the at least one stripe is completely enclosed within the matrix material.

3. The tubular member of claim 1 wherein the body has an outer surface, at least a portion of the at least one stripe extending radially outward from the outer surface of the body.

4. The tubular member of claim 1 wherein the balloon defines a lumen, at least a portion of the at least one stripe extending radially inward from the matrix material into the lumen.

5. The tubular member of claim 1 wherein the at least one stripe has a thickness and width equal to that of the matrix material.

6. The tubular member of claim 1 wherein the second material has a durometer value different than that of the matrix material.

7. The tubular member of claim 1 wherein the at least one stripe is helically disposed relative to the body.

8. The tubular member of claim 1 wherein the at least one stripe is longitudinally disposed relative to the body.

9. The tubular member of claim 1 wherein the at least one stripe increases in circumferential width as it extends from the first cone region toward the second cone region.

10. The tubular member of claim 9 wherein the at least one stripe is a plurality of stripes, at least a portion of each stripe converging to form a uniform ring of the second material.

11. The tubular member of claim 1 wherein least one stripe has a varied radial thickness.

12. The tubular member of claim 1 wherein the tubular member is a balloon catheter.

13. A stent delivery system comprising:
a balloon catheter, the balloon catheter comprising a balloon, the balloon having a body portion positioned between a first cone region and a second cone region, the body portion constructed from an extruded matrix material and at least one stripe of a second material, the second material being softer than the matrix material and at least partially contained within the matrix material, the first cone region and the second cone region being constructed from the matrix material; and a stent, the stent being expandable from an unexpanded state to an expanded state, in the unexpanded state the stent being removably mounted to at least a portion of the body portion of the balloon.

* * * * *